United States Patent [19]
Milkowski et al.

[11] 3,969,356
[45] July 13, 1976

[54] N-[3-(P-F-BENZOYL)-PROPYL]-N'-[2.(NI-TRO,NITRO-EL, OR METHOXYPHENYL)-ETHYL]-PIPERAZINES

[75] Inventors: Wolfgang Milkowski, Burgdorf;
Horst Zeugner, Hannover;
Klaus-Wolf von Eickstedt,
Isernhagen N.B.; Werner Stühmer,
Eldagsen, all of Germany

[73] Assignee: Kali-Chemie Aktiengesellschaft,
Hannover, Germany

[22] Filed: June 20, 1975

[21] Appl. No.: 589,121

Related U.S. Application Data

[63] Continuation of Ser. No. 288,320, Sept. 12, 1972, abandoned.

[30] Foreign Application Priority Data

Sept. 13, 1971 Germany............................ 2145682
July 26, 1972 Germany............................ 2236680

[52] U.S. Cl............................... 260/268 R; 424/250; 424/244; 260/239 BC
[51] Int. Cl.²....................................... C07D 295/10
[58] Field of Search............................... 260/268 R

[56] References Cited
UNITED STATES PATENTS

| | | | |
|---|---|---|---|
| 2,695,293 | 11/1954 | Swain.............................. | 260/268 R |
| 2,695,295 | 11/1954 | Swain.............................. | 260/268 R |
| 3,000,892 | 9/1961 | Janssen............................ | 260/268 R |
| 3,637,704 | 1/1972 | Umemoto......................... | 260/268 R |

FOREIGN PATENTS OR APPLICATIONS 2,027,054   6/1970   Germany......................... 260/268 R

*Primary Examiner*—Alton D. Rollins
*Assistant Examiner*—Jose Tovar
*Attorney, Agent, or Firm*—Michael J. Striker

[57] ABSTRACT

1,4-diazacycloalkane derivatives of the formula

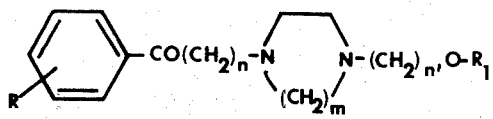

wherein

R is hydrogen, halogen, lower alkoxy, nitro or lower secondary amine, $R_1$ is lower alkoxyphenyl, nitrophenyl or trifluoromethylphenyl or wherein $R_1$ is phenyl, that is disubstituted by two halogen, by two lower alkyl, by halogen and nitro, by halogen and lower alkyl, by halogen and lower alkoxy or by lower alkoxy and lower alkoyl, lower in these definitions meaning from 1 to 4 carbon atoms and wherein $n$, $n'$ and $m$ are 2 or 3;

and pharmaceutically acceptable acid addition products of these compounds.

The compounds are sedatives with an analgesic and anti-histaminic effect and possess a low toxicity.

7 Claims, No Drawings

N-[3-(P-F-BENZOYL)-PROPYL]-N'-[2.(NITRO,NITRO-EL, OR METHOXYPHENYL)-ETHYL]-PIPERAZINES

CROSS REFERENCE TO RELATED APPLICATION

This application is a continuation of our prior application Ser. No. 288,320, filed Sept. 12, 1972, now abandoned.

SUMMARY OF THE INVENTION

The invention lies in sedatives having an analgesic and anti-histaminic effect and consisting of 1,4-diazacycloalkane derivatives of the formula

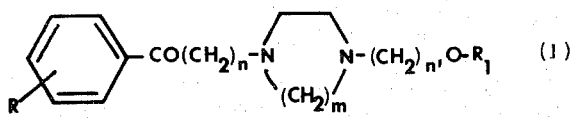

wherein
R is hydrogen, halogen, lower alkoxy, nitro or lower secondary amine,
$R_1$ is lower alkoxyphenyl, nitrophenyl or trifluoromethylphenyl or wherein $R_1$ is phenyl, that is disubstituted by two halogen, by two lower alkyl, by halogen and nitro, by halogen and lower alkyl, by halogen and lower alkoxy or by lower alkoxy and lower alkoyl, lower in these definitions meaning 1 to 4 carbon atoms and wherein
$n$, $n'$ and $m$ are 2 or 3;
and pharmaceutically acceptable acid addition products of these compounds.

The invention also comprises a process of making the compounds by reacting a piperazine or homopiperazine of the formula

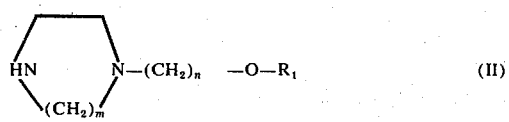

in which $n'$, $m$ and $R_1$ have the meaning above given with formaldehyde and an acetophenone of the formula

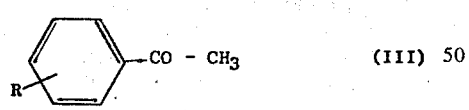

wherein R has the meaning as above in the presence of a mineral acid at an elevated temperature, which usually is between 50° and 150°C, and finally isolating the salt thus obtained from the reaction mixture whereupon the free base may then be obtained.

DETAILS OF THE INVENTION AND SPECIFIC EMBODIMENTS

The compounds of the invention have been identified in the above summary of the invention. It is noted that the term "lower" throughout implies specifically groups having 1 to 4 carbon atoms. Where R is secondary amino it may also be a cyclic amino group.

The mineral acid used in carrying out the main reaction may for instance be hydrochloric acid. The reaction should take place at elevated temperature which usually should be between 50° and 150°C.

The diazacycloalkane of formula II above given which is used as starting product may also be employed in the form of the dihydrochloride and may thus furnish the hydrochloric acid necessary for the reaction.

It may be useful in many cases to carry out the reaction in a polar solvent such as ethanol or propanol.

For making the diazacycloalkane derivatives in which n is 2 or 3 the compounds of the above given formula II can be reacted with ω-halogenoalkylketones of the formula

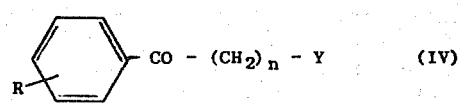

in which R and $n$ have the same meaning as given in the above summary and Y is halogen, preferably chlorine. This reaction is carried out at an elevated temperature in the presence of a basic condensing agent, such as, a tertiary amine, like triethylamine, or in the presence of sodium carbonate, sodium bicarbonate and preferably potassium carbonate. As the acid acceptor there may also be used an excess of the amine employed in the reaction.

The reaction can be carried out in an inert solvent at the boiling point of the solvent. Solvents may for instance be xylene, toluene, n-butanol or methylisobutylketone. In order to obtain the desired compound it is advisable to convert the crude base obtained in the reaction into an acid addition compound, for instance the dihydrochloride, from which the pure base may then be obtained if desired.

The reaction between a compound of the above formula II with a γ-halogenobutyrophenone coming under the formula IV above in an inert solvent in the presence of a basic condensing agent may be carried out under milder conditions and with a better yield if prior to the main reaction the γ-halogenobutyrophenone is first reacted with ethyleneglycol under acidic conditions in order to protect the keto group. Thus the corresponding γ-halogenobutyroketal of the formula

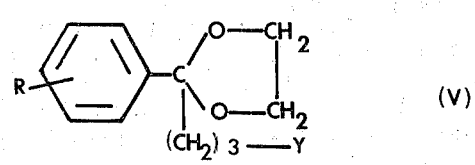

is formed. The desired compound of formula I is then obtained by splitting off the ketal group with dilute hydrochloric acid after completion of the reaction. The final compound can then be isolated in the form of its dihydrochloride.

In order to obtain compounds as defined in formula I in which R is secondary amine it is preferred to employ as starting products compounds in which R is a halogen atom, preferably fluorine and react these compounds with a secondary amine in a polar solvent, preferably dimethylsulfoxide at an elevated temperature.

The acid used to obtain the non-toxic acid addition salts may be any pharmaceutically acceptable acid. Preferred are for instance acetic acid, propionic acid, diethyl acetic acid, malonic acid, succinic acid, fumaric acid, maleic acid, lactic acid, tartaric acid, malic acid, citric acid, sulfuric acid, hydrobromic acid or orthophosphoric acid. These acid addition compounds can be used for the pharmaceutical purposes of the invention like the free base and they have the advantage that they are soluble in water.

UTILITY

The compounds of the invention unexpectedly constitute sedatives with an analgesic action and anti-histaminic effects. They are of low toxicity.

They are useful for the treatment of patients requiring mental treatment. They may be applied per os or parenterally particularly by subcutaneous injection.

Water soluble compositions may be formed by dissolving the pharmaceutically acceptable salts of the compounds in aqueous solutions. Water insoluble solutions may be prepared for instance in a 1% methylcellulose suspension.

The general dosage range appears from the tests below. It may be adjusted in the customary way for use on human patients.

In order to determine the activity of the following compounds of the invention which are described hereinafter in the Examples specified tests were set up employing comparative compounds which are in general use for similar purposes:

1. $N_1$-[3-(4'-fluorobenzoyl)-propyl]-$N_2$-[2-(4'-nitrophenoxy)-ethyl]-piperazine dihydrochloride hydrate (Examples 1 and 2)

2. $N_1$-[3-(4'-fluorobenzoyl)-propyl]-$N_2$-[2-(2'-chloro-5'-methylphenoxy)-ethyl]-piperazine dihydrochloride (Example 5)

3. $N_1$-[3-(4'-fluorobenzoyl)-propyl]-$N_2$-[2-(4' methoxyphenoxy)-ethyl]-piperazine dihydrochloride. (Example 6)

4. $N_1$-[3-(4'-fluorobenzoyl)-propyl]-$N_2$-[2-(2'-nitrophenoxy)-ethyl]-piperazine dihydrochloride. (Example 12)

5. $N_1$-[3-(4'-fluorobenzoyl)-propyl]-$N_2$-[2-(3'-nitrophenoxy)-ethyl]-piperazine dihydrochloride. (Example 13)

6. $N_1$-(3-benzoylpropyl)-$N_2$-[2-(4'--methoxy-phenoxy)-ethyl]-piperazine dihydrochloride. (Example 8)

7. $N_1$-[3-(4'-fluorobenzoyl)-propyl]-$N_2$-[3-(4'-nitrophenoxy)-propyl]-piperazine dihydrochloride. (Example 14)

8. $N_1$-(3-benzoylpropyl)-$N_2$-[2-(4'-nitrophenoxy)-ethyl]-piperazine dihydrochloride. (Example 9)

The mean lethal dose ($LD_{50}$) was determined by administration of the compound per os to male albino mice of genus NMRI. The results appear from the Table below.

The analgesic action of the compounds was determined in the Writhing test. Employing the method described by E. Sigmund, R. Cadmus and G. Lu in Proc. Soc. exp. Biol., N.Y. 95 (1957), page 729 the compounds were administered to albino mice as just mentioned. After 30 minutes 1.5 mg of phenyl quinone per kg of body weight were administered into the abdominal cavity of the test animals. As comparison compounds 100 mg per kg of aminopyrine (4-dimethylamino-2,3-dimethyl-1-phenyl-3-pyrazolin-5-one) and 14.7 mg per kg of morphine per os were used.

In the Table I below the amounts are given of the foregoing compounds of the invention referred to by the number assigned hereinbefore in mg/kg which when administered per os have the same effect as the listed doses of the comparison compounds.

TABLE 1

| Test Compound No. | $LD_{50}$ mg/kg | Writhing Test 100 mg/kg aminopyrine mg/kg | 14.7 mg/kg morphine mg/kg | 300% extension of duration of barbital-induced sleep mg/kg |
|---|---|---|---|---|
| 1 | 215 | 7.0 | 10.0 | 2.2 |
| 2 | 464 | 6.0 | 10.0 | 10.0 |
| 3 | 215 | 4.0 | 10.0 | 10.0 |
| 4 | 415 | 31.6 | 68.0 | not determined |
| 5 | 316 | 6.0 | 14.7 | 10.0 |
| 6 | 249 | 14.7 | 21.5 | 21.5 |

The Table shows that the compounds of the invention have a strong action on the typical reflexes of the mice in the Writhing test and also have a high analgesic effect.

In addition the compounds of the invention have an action in extending hexobarbital induced sleep in mice. To determine this action the compounds listed in Table 2 below were administered per os 30 minutes prior to the administration of the hexobarbital. The amount given in the last column in each case is the amount of the particular compound expressed in mg per kg of body weight which causes an extension of the duration of the hexobarbital induced sleep by 300%.

The action of the compounds of the invention in respect to the motion activity of mice was determined employing the method described by H. Weifenbach in Arzneimittel Forschung 19 (1969), pp. 125 to 127, using the squirrel cage test, It was found that the running mobility of the mice was clearly depressed by oral administration of the compounds of the invention.

As comparison compound in the following test chlorpromazine was administered per os at a dose of 3.2 mg per kg of body weight. In the test that dose of the compounds of the invention was determined which caused the same reduction of the running activity as the mentioned dose of chlorpromazine. The results appear from the Table 2 below.

TABLE 2

| Comparison compound: | Chlorpromazine dose 3.2 mg/kg |
|---|---|
| Test compound No. | mg/kg |
| 1 | 3.2 |
| 2 | 3.2 |
| 3 | 3.2 |
| 5 | 3.2 |
| 6 | 10.0 |
| 7 | 10.0 |
| 8 | 3.2 |

The invention is further illustrated by the following Examples:

EXAMPLE 1

$N_1$-[3-(4'-fluorobenzoyl)-propyl]-$N_2$-[2-(4'-nitrophenoxy)-ethyl]-piperazine dihydrochloride hydrate.

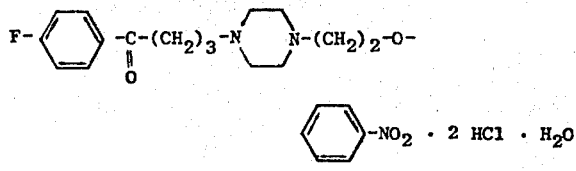

39.2 g of N-[2-(4'-nitrophenoxy)-ethyl]-piperazine and 31.2 g of 4-fluoro-γ-chlorobutyrophenone were heated on an oil bath for 6 hours to 120° to 130°C. The reaction mass was cooled to 70°C and was then taken up in a small amount of benzene and filtered over 500 g of aluminum oxide (III) according to the Brockmann method. After evaporation of the solvent there were obtained 40 g of crude base. The base was dissolved in ethanol and converted with HCl gas to the dihydrochloride. The salt was separated by filtration and recrystallized from ethanol with 20% water. There was thus obtained the dihydrochloride hydrate at a yield of 28.3 g. The melting point was between 223° and 225°C.

EXAMPLE 2

$N_1$-[3-(4'-fluorobenzoyl)-propyl]-$N_2$-[2-(4'-nitrophenoxy)-ethyl]-piperazine dihydrochloride hydrate This example illustrates a slightly different process for obtaining the same compound as is described in Example 1.

23 g of N-[2-(4'-nitrophenoxy)-ethyl]-piperazine and 19 g of 4-fluoro-γ-chlorobutyrophenone were subjected to boiling at reflux in 300 ml xylene with 15 g of potassium carbonate for a time of 24 hours. The solution was then filtered while hot. Thereafter about 150 ml of xylene were distilled off. The residue was dissolved in 50 ml benzene over about 400 g of aluminum oxide (III) by employing benzene for the elution. After distilling off the benzene 17.1 g of crude base were obtained which in the manner described in Example 1 were converted in an ethanol solution to the dihydrochloride hydrate. The yield was 11.9 g. The compound had a melting point between 224° and 226°C. No lowering of the melting point of the product obtained according to Example 1 could be observed.

EXAMPLE 3

$N_1$-[2-(4'-nitrobenzoyl-ethyl]-$N_2$-[2-(4'-nitro phenoxy)-ethyl]-piperazine dimaleate

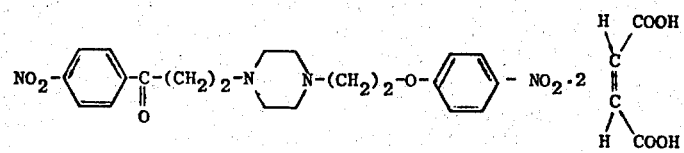

32.4 g of N-(2-nitrophenoxy)-ethyl-piperazine-dihydrochloride and 14.9 g of p-nitroacetophenone were heated to boiling point at reflux with 6 g of paraformaldehyde in 300 ml isopropanol for a time of 24 hours. The separated crystals were removed by filtration and recrystallized from ethanol/water. The crystals were dissolved in a little water. While cooling with ice the mass was reacted with an excess of ice cold 10% ammonia solution. The separated base was taken up in methylene chloride and dried with sodium sulfate. After distilling off the solvent the residue was reacted in ethanol with 2 equivalents of maleic acid. The separated crystals were recrystallized from ethanol. The yield was 3.4 g. The melting point as 173°C.

EXAMPLE 4

$N_1$-[3-(4'-morpholinobenzoyl)-propyl]-$N_2$-[2-(4'-nitro phenoxy)-ethyl]-piperazine dihydrochloride hydrate

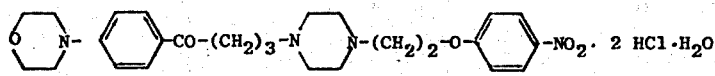

21.5 g of $N_1$-[3-(4'-fluorobenzoyl)-propyl]-$N_2$-[2-(4'-nitrophenoxy)-ethyl]-piperazine were heated in 100 ml dimethylsulfoxide with 4.5 g of morpholine to 100°C for 24 hours. The solution was then poured on ice water and thoroughly extracted with methylene chloride. The organic solution was thereafter dried whereupon the solvent was distilled off. The residue was dissolved in 50 ml of benzene and filtered over 300 g aluminum oxide (III) by employing benzene for the elution. After evaporation of the solvent the dihydrochloride was obtained from the residue as described in Example 1 and subjected to recrystallization from ethanol/water. The yield was 14.7 g. The melting point was 240° to 242°C.

EXAMPLE 5

$N_1$-[3-(4'-fluorobenzoyl)-propyl]-$N_2$-[2-(2'-chloro-5'-methylphenoxy)ethyl]-piperazine dihydrochloride

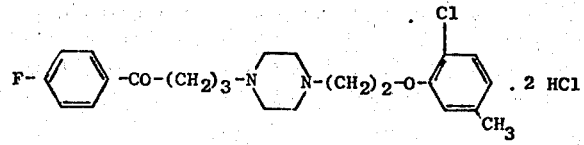

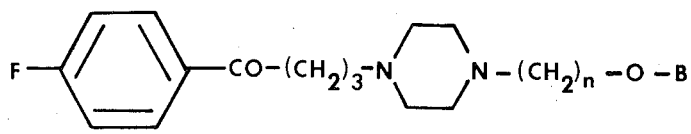

6.1 g of N-[2-(2'-chloro-5'-methylphenoxy)-ethyl]-piperazine, 6.4 g of 4-(p-fluorophenyl)-4,4-ethylendioxy-1-chlorbutane, 5 g of potassium carbonate and 2.9 g of potassium bromide were heated to boiling point under reflux in 100 ml methylisobutylketone for 36 hours. The hot solution was then filtered. After cooling down the filtrate was stirred with 10% hydrochloric acid. The dihydrochloride thereby precipitated as a white crystalline precipitate. The salt was removed by filtration and recrystallized from ethanol/water. The yield was 7 g. The melting point of the compound was between 227° and 230°C.

The same process was then used employing corresponding starting compounds to make the compounds identified as Examples 6 to 40 listed in the following Table 3.

TABLE 3

$$R\text{—}C_6H_4\text{—}CO(CH_2)_n\text{—}N\underset{(CH_2)_m}{\diagup\diagdown}N\text{—}(CH_2)_{n'}\text{—}O\text{—}R_1$$

| Ex. | R | n | n' | m | $R_1$ | salt | m.p.(°C) |
|---|---|---|---|---|---|---|---|
| 6 | 4-F | 3 | 2 | 2 | $4\text{-}H_3CO\text{—}C_6H_4$ | 2 HCl | 204–207 |
| 7 | 4-Cl | 3 | 2 | 2 | $4\text{-}H_3CO\text{—}C_6H_4$ | 2 HCl | 224–226 |
| 8 | H | 3 | 2 | 2 | $4\text{-}H_3CO\text{—}C_6H_4$ | 2 HCl | 199–200 |
| 9 | H | 3 | 2 | 2 | $4\text{-}O_2N\text{—}C_6H_4$ | 2 HCl | 240 |
| 10 | H | 3 | 3 | 2 | $4\text{-}O_2N\text{—}C_6H_4$ | 2 HCl | 236–258 |
| 11 | $4\text{-}H_5CO$ | 2 | 2 | 2 | $4\text{-}O_2N\text{—}C_6H_4$ | 2 HCl | 197–198 |
| 12 | 4-F | 3 | 2 | 2 | $2\text{-}O_2N\text{—}C_6H_4$ | 2 HCl | 230–231 |
| 13 | 4-F | 3 | 2 | 2 | $3\text{-}O_2N\text{—}C_6H_4$ | 2 HCl | 226–228 |
| 14 | 4-F | 3 | 3 | 2 | $4\text{-}O_2N\text{—}C_6H_4$ | 2 HCl | 235–237 |
| 15 | 4-Cl | 3 | 2 | 2 | $4\text{-}O_2N\text{—}C_6H_4$ | 2 HCl | 228 |
| 16 | 4-F | 3 | 2 | 2 | $4\text{-}O_2N/2\text{-}Cl\text{—}C_6H_3$ | 2 HCl | 218–220 |
| 17 | 4-Cl | 3 | 2 | 2 | $4\text{-}O_2N/2\text{-}Cl\text{—}C_6H_3$ | 2 HCl | 220–221 |
| 18 | H | 3 | 2 | 2 | $4\text{-}O_2N/2\text{-}Cl\text{—}C_6H_3$ | 2 HCl | 215 |
| 19 | 4-F | 3 | 2 | 3 | $4\text{-}O_2N\text{—}C_6H_4$ | dimaleate | 153 |
| 20 | 4-F | 3 | 2 | 2 | $2\text{-}O_2N/4\text{-}Cl\text{—}C_6H_3$ | 2 HCl | 233 |
| 21 | 4-F | 3 | 2 | 2 | $3\text{-}H_3CO\text{—}C_6H_4$ | 2 HCl/$C_2H_5$OH | 189–191 |
| 22 | 4-F | 3 | 2 | 2 | $2\text{-}H_3CO\text{—}C_6H_4$ | 2 HCl | 196–197 |
| 23 | 4-Cl | 3 | 2 | 2 | $2\text{-}H_3CO\text{—}C_6H_4$ | 2 HCl | 200–202 |
| 24 | 4-Cl | 3 | 2 | 2 | $2\text{-}O_2N\text{—}C_6H_4$ | 2 HCl | 245 |
| 25 | 4-F | 3 | 2 | 2 | $4\text{-}Cl/3\text{-}CH_3\text{—}C_6H_3$ | 2 HCl | 219–221 |
| 26 | H | 3 | 2 | 2 | $2\text{-}H_3CO\text{—}C_6H_4$ | 2 HCl | 198–199 |
| 27 | H | 3 | 2 | 2 | $2\text{-}O_2N\text{—}C_6H_4$ | 2 HCl | 233–235 |
| 28 | 4-F | 3 | 2 | 2 | $4\text{-}Cl/2\text{-}CH_3\text{—}C_6H_3$ | 2 HCl/$C_2H_5$OH | 235 |
| 29 | 4-F | 3 | 2 | 2 | $4/2\text{-}Cl\text{—}C_6H_3$ | 2 HCl | 245 |
| 30 | 4-F | 3 | 2 | 2 | $4/3\text{-}Cl\text{—}C_6H_3$ | 2 HCl/$C_2H_5$OH | 230 |
| 31 | 4-F | 3 | 2 | 2 | $3\text{-}CF_3\text{—}C_6H_4$ | 2 HCl | 235–237 |
| 32 | 4-F | 3 | 2 | 2 | $3/2\text{-}Cl\text{—}C_6H_3$ | 2 HCl | 249–250 |
| 33 | 4-F | 3 | 2 | 2 | $3/5\text{-}Cl\text{—}C_6H_3$ | 2 HCl | 237–240 |
| 34 | 4-F | 3 | 2 | 2 | $3/2\text{-}CH_3\text{—}C_6H_3$ | 2 HCl/$C_2H_5$OH | 245–246 |
| 35 | 4-F | 3 | 2 | 2 | $2/5\text{-}CH_3\text{—}C_6H_3$ | 2 HCl | 248–250 |
| 36 | 4-F | 3 | 2 | 2 | $3/5\text{-}CH_3\text{—}C_6H_3$ | 2 HCl | 246 |
| 37 | 4-F | 3 | 2 | 2 | $2/6\text{-}CH_3\text{—}C_6H_3$ | 2 HCl | 240–242 |
| 38 | 4-F | 3 | 2 | 2 | $3/4\text{-}CH_3\text{—}C_6H_3$ | 2 HCl | 240 |
| 39 | 4-F | 3 | 2 | 2 | $3\text{-}Cl/5\text{-}CH_3O\text{—}C_6H_3$ | 2 HCl | 224–226 |
| 40 | 4-F | 3 | 2 | 2 | $2\text{-}CH_3O/4\text{-}CH_3\text{—}\underset{\parallel}{\underset{O}{C}}\text{—}C_6H_3$ | 2 HCl/$H_2O$ | 232–234 |

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A compound having the formula in which
n is 2, and
B is a mononitrophenyl, monochloronitrophenyl, or methoxyphenyl moiety, or a pharmaceutically acceptable acid addition salt thereof.

2. A compound as defined in claim 1 in which B is a 2-nitrophenyl, 3-nitrophenyl, 4-nitrophenyl, 2-methoxyphenyl, 3methoxyphenyl, 4methoxyphenyl, or 2-chloro-4nitrophenyl, moiety, or a pharmaceutically acceptable acid addition salt thereof.

3. A compound as defined in claim 1 which is $N_1$-[3-(4-fluorobenzoyl)propyl]-$N_2$-[2-nitrophenoxy)ethyl]-piperazine.

4. A compound as defined in claim 1 which is $N_1$-[3-(4-fluorobenzoyl)propyl]-$N_2$-[2-(4-methoxyphenoxy)-ethyl]piperazine.

5. A compound as defined in claim 1 which is $N_1$-[3-(4-fluorobenzoyl)propyl]-$N_2$-[2-(3-nitrophenoxy)ethyl]piperazine.

6. A compound as defined in claim 1 which is $N_1$-[3-(4-fluorobenzoyl)propyl]-$N_2$-[2-(2-chloro-4-nitrophenoxy)ethyl]piperazine.

7. A compound as defined in claim 1 which is $N_1$-[3-(4-fluorobenzoyl)propyl]-$N_2$-[2-(3-methoxyphenoxy)ethyl]piperazine.

* * * * *

UNITED STATES PATENT AND TRADEMARK OFFICE
CERTIFICATE OF CORRECTION

PATENT NO. : 3,969,356
DATED : July 13, 1976
INVENTOR(S) : Wolfgang Milkowski et al It is certified that error appears in the above-identified patent and that said Letters Patent are hereby corrected as shown below:

IN THE TITLE [54]

The title should read as follows:

"N-[3-(P-F-BENZOYL)-PROPYL]-N'-[2-(NITRO, NITRO-CL, OR METHOXYPHENYL)-ETHYL]-PIPERAZINES"

IN THE SPECIFICATION

Column 1, line 40, "$(CH_2)n$" should read -- $(CH_2)n'$ --.
Column 3, line 54, "-(4' me-" should read -- (4'-me- --.

IN THE CLAIMS

Claim 2, column 8, lines 15 and 16, a dash should be present after the numerals "3" and "4", respectively.

Claim 3, column 8, line 19, "-$N_2$-[2-nitrophenoxy)ethyl]-" should read -- -$N_2$-[2-(4-nitrophenoxy)ethyl]- --.

Signed and Sealed this

First Day of February 1977

[SEAL]

Attest:

RUTH C. MASON
*Attesting Officer*

C. MARSHALL DANN
*Commissioner of Patents and Trademarks*